United States Patent
Rodzevski et al.

(10) Patent No.: US 9,489,511 B2
(45) Date of Patent: Nov. 8, 2016

(54) WEARABLE DEVICE AND A METHOD FOR STORING CREDENTIALS ASSOCIATED WITH AN ELECTRONIC DEVICE IN SAID WEARABLE DEVICE

(71) Applicant: Sony Mobile Communications Inc., Tokyo (JP)

(72) Inventors: Aleksandar Rodzevski, Malmö (SE); Henrik Bengtsson, Lund (SE); Dragan Dimovski, Eslöv (SE)

(73) Assignees: Sony Corporation, Tokyo (JP); Sony Mobile Communications AB, Tokyo (JP)

( * ) Notice: Subject to any disclaimer, the term of this patent is extended or adjusted under 35 U.S.C. 154(b) by 62 days.

(21) Appl. No.: 14/533,492

(22) Filed: Nov. 5, 2014

(65) Prior Publication Data

US 2015/0161377 A1 Jun. 11, 2015

Related U.S. Application Data

(60) Provisional application No. 61/912,223, filed on Dec. 5, 2013.

(51) Int. Cl.
| | | |
|---|---|---|
| *G06F 21/45* | (2013.01) | |
| *G06F 21/35* | (2013.01) | |
| *H04L 29/06* | (2006.01) | |
| *A61B 5/024* | (2006.01) | |
| *A61B 5/01* | (2006.01) | |
| *A61B 5/026* | (2006.01) | |
| *A61B 5/11* | (2006.01) | |

(52) U.S. Cl.
CPC .............. *G06F 21/45* (2013.01); *G06F 21/35* (2013.01); *H04L 63/0853* (2013.01); *A61B 5/01* (2013.01); *A61B 5/026* (2013.01); *A61B 5/02438* (2013.01); *A61B 5/1101* (2013.01)

(58) Field of Classification Search
None
See application file for complete search history.

(56) References Cited

U.S. PATENT DOCUMENTS

| | | |
|---|---|---|
| 6,211,799 B1 | 4/2001 | Post et al. |
| 6,580,356 B1 | 6/2003 | Alt et al. |
| 7,202,773 B1 | 4/2007 | Oba et al. |
| 8,867,995 B2 | 10/2014 | Kim et al. |
| 2002/0128030 A1 | 9/2002 | Eiden et al. |
| 2004/0203381 A1 | 10/2004 | Cahn et al. |

(Continued)

FOREIGN PATENT DOCUMENTS

| | | |
|---|---|---|
| EP | 1024626 A1 | 8/2000 |
| EP | 1102215 A2 | 5/2001 |

(Continued)

OTHER PUBLICATIONS

"The NYMI White Paper", Nov. 19, 2013, XP055115588, pp. 3,5,6,14-21.

(Continued)

*Primary Examiner* — Minh Dinh
(74) *Attorney, Agent, or Firm* — Tucker Ellis LLP

(57) ABSTRACT

The disclosure relates in general to a wearable device for serving as a personal id towards electronic devices. In particular the disclosure provides a wearable device for storing credential data or password from an electronic device, which device is configured for serving as personal id towards an electronic device, such as a mobile phone or other smart devices.

8 Claims, 7 Drawing Sheets

(56) References Cited

U.S. PATENT DOCUMENTS

| | | |
|---|---|---|
| 2004/0248513 A1 | 12/2004 | Glass et al. |
| 2005/0008148 A1 | 1/2005 | Jacobson |
| 2005/0243061 A1 | 11/2005 | Liberty et al. |
| 2006/0109135 A1 | 5/2006 | Donat et al. |
| 2006/0258408 A1 | 11/2006 | Tuomela et al. |
| 2007/0145119 A1 | 6/2007 | Rhelimi |
| 2007/0190940 A1 | 8/2007 | Lee et al. |
| 2007/0282783 A1 | 12/2007 | Singh |
| 2008/0259043 A1 | 10/2008 | Buil et al. |
| 2009/0094681 A1 | 4/2009 | Sadler et al. |
| 2009/0233548 A1 | 9/2009 | Andersson et al. |
| 2010/0003917 A1 | 1/2010 | Hebiguchi et al. |
| 2010/0113950 A1 | 5/2010 | Lin et al. |
| 2010/0263031 A1 | 10/2010 | Tsuchiya |
| 2010/0277435 A1 | 11/2010 | Han et al. |
| 2010/0311326 A1 | 12/2010 | Klabunde et al. |
| 2010/0312071 A1 | 12/2010 | Schenk |
| 2011/0205156 A1 | 8/2011 | Gomez et al. |
| 2012/0026129 A1 | 2/2012 | Kawakami |
| 2012/0133605 A1 | 5/2012 | Tanaka |
| 2012/0249409 A1 | 10/2012 | Toney et al. |
| 2012/0324368 A1 | 12/2012 | Putz et al. |
| 2013/0017789 A1 | 1/2013 | Chi et al. |
| 2013/0174049 A1 | 7/2013 | Townsend et al. |
| 2014/0085050 A1 | 3/2014 | Luna |
| 2014/0325614 A1 | 10/2014 | Rhelimi |
| 2015/0135310 A1* | 5/2015 | Lee .................. A61B 5/681 726/20 |

FOREIGN PATENT DOCUMENTS

| | | |
|---|---|---|
| EP | 1220501 A2 | 7/2002 |
| EP | 2018038 A2 | 1/2009 |
| EP | 2378748 A1 | 10/2011 |
| EP | 2600319 A1 | 6/2013 |
| JP | 2008073462 A | 4/2008 |
| JP | 2009049951 A | 3/2009 |
| WO | 2007096810 A1 | 8/2007 |
| WO | 2007129237 A1 | 11/2007 |
| WO | 2011021531 A1 | 2/2011 |

OTHER PUBLICATIONS

Bionym Inc: "Nymi by Bionym" Sep. 2, 2013, YouTube Video retrieved from the Internet May 7, 2014 at URL: https://www.youtube.com/watch?v=jUO7Qnmc8vE#t=37.

PCT International Search Report issued on May 9, 2014 for the corresponding international application No. PCT/Ib/2014/000007, 4 pages.

W. Knight, "Human Handshake Opens Data Stream," NewScientist.com, Oct. 7, 2002, http://www.newscientist.com/article/dn2891-human-handshake-opens-data-stream.html.

W. Knight, "Skin Used to Transmit Key Data," NewScientist.com, Aug. 5, 2004, http://www.newscientist.com/article/dn6247-skin-used-to-transmit-key-data.html.

* cited by examiner

WEARABLE DEVICE AND A METHOD FOR STORING CREDENTIALS ASSOCIATED WITH AN ELECTRONIC DEVICE IN SAID WEARABLE DEVICE

RELATED APPLICATION

This application claims priority under 35 U.S.C. §119, based on U.S. Provisional Application No. 61/912,223, filed Dec. 5, 2013, the disclosure of which is hereby incorporated by reference herein.

TECHNICAL FIELD

The disclosure relates in general to a wearable device for storing credentials associated with electronic devices. In particular the disclosure provides for a wearable device and a method for storing credential data, such as a password associated with an electronic device.

BACKGROUND ART

Many portable devices, such as for example, mobile phones, hand-held computers, personal digital assistants (PDAs), etc. have become the hub for lots of private and corporate information and the loss if a portable device is stolen is worth more than just the hardware itself. When portable devices are used for transactions and payments the importance of protecting its content increases even further. Many people protect their portable devices with credential data such as a 4-6 digit key or password, or a graphical pattern, and it is generally seen as too short and too easy to break. Longer passwords are possible to use, however, many people consider it cumbersome to do the unlock procedure every time the portable device is used. Yet many people have no protection at all.

Credential data is a proof of qualification, competence or clearance issued to an individual. Examples of credentials include, certifications, security clearance, identification documents, badges, passwords, user names, keys, and so on. Credentials in information technology systems, IT systems, are widely used to control access to information or other resources. The classic combination of a user account number or name and a secret password is widely used example of IT systems credentials. An increasing number of IT systems use other forms of documentation of credentials, such as biometric credential technologies. There are several examples of biometric credential technologies that could be used for this purpose such as fingerprints, face and voice recognition, iris recognition or retinal scans, and so on. It is basically up to the user to determine the level of security needed for that particular case.

A biometric method that is known is to use a fingerprint scanner that is arranged under the home screen displayed on an electronic device. However, such a solution can be cumbersome for the user, since the user may have to use the same finger every time the user logs on to the device. Furthermore, using fingerprint is slightly slower than just pressing the button and it does not work with gloves. However, although the fingerprint scanning has a given security level, it may not be high enough for certain operations and the users are reluctant to give away their biometrics.

Another biometric method that is known is to use a wristband which does heartbeat identification (ECG). The identification is done by closing the wristlet around an arm of the user, and then a finger from the other hand of the user is put on the wristband which closes a loop around the heart. Thereby the ECG can be detected. The user will automatically be able to logon to a mobile phone once a setup is done. However, although the fingerprint scanning has a given security level, it may not be high enough for certain operations and the users are reluctant to give away their biometrics.

Hence, the security level on the identification means of today does not fulfill all requirements.

SUMMARY OF THE INVENTION

With the above description in mind, then, an aspect of some embodiments of the present invention is to provide a wearable device for serving as a personal identification device for a user towards electronic devices, such as a mobile phone or other smart devices, and a method for performing the same, and this seeks to mitigate, alleviate or eliminate one or more of the above-identified deficiencies in the art and disadvantages singly or in any combination.

An aspect of the present invention relates to a wearable device for temporarily storing credential data associated with at least one electronic device comprising:
 a detector unit configured for detecting the presence of a human body;
 a radio communication interface configured to communicate with the at least one electronic device;
 a data storage configured to store the credential data;
 a processing circuitry configured:
 to broadcast a signal, indicating an ability to temporarily store credential data, when said detector unit detects the presence of a human body;
 to receive, using the radio communication interface, the credential data from said electronic device;
 to store, in the data storage, the received credential data in the data storage as long as said detector unit detects the presence of a human body, and
 to transmit the credential data to the electronic device, when a request for credentials is received.

According to one aspect the device further comprises that the processing circuitry is configured to delete the credential data when the presence of a human body is no longer detected.

According to one aspect the device further comprises that the processing circuitry is configured to receive encrypted credential data.

According to one aspect the device further comprises an electronic module and a wearable unit. According to one aspect the device further comprises that the electronic module comprises the radio communication interface, said data storage and said processing circuitry. According to one aspect the device further comprises that the electronic module further comprises said detector unit.

Another aspect of the present invention relates to a method, performed in a wearable device, of temporarily storing credentials associated with at least one electronic device within the wearable device, the method comprising the steps of:
 broadcasting a signal, indicating an ability to temporarily store credential data, when the presence of a human body is detected by a detector unit;
 receiving, using a radio communication interface, credential data from said electronic device,
 storing, in a data storage, the received credentials in the data storage as long as said detector unit detects the presence of a human body, and transmitting the credential data to the electronic device, when a request for credential data is received.

According to one aspect the method further comprises the step of deleting the credential data when the presence of a human body is no longer detected.

Another aspect of the present invention relates to a method, performed in an electronic device, of temporarily storing credential data associated with said electronic device in a wearable device, the method comprising the steps of:

detecting a request for unlocking said electronic device;

identifying if authentication is needed;

receiving credential data from wearable device when opening the electronic device.

According to one aspect the method the receiving step further comprises the steps of:

identifying if credential data is stored in wearable device;

sending request for credential data from wearable device;

receiving credential data from wearable device.

According to one aspect the method the receiving step further comprises the steps of:

identifying if credential data is stored in wearable device, and receiving credential data from input device of said electronic device.

According to one aspect the method further comprises the step of detecting a wearable device with ability to temporarily store credential data.

According to one aspect the method further comprising the steps of:

detecting a broadcast signal, indicating an ability to temporarily store credential data, sending request for permission to create a connection between said electronic device and said wearable device (1), sending credential data to said wearable device (1) for storage in said device.

According to one aspect the method further comprises the steps of creating a communication channel between electronic device and wearable device.

The features of the above-mentioned embodiments can be combined in any combinations.

It is an advantage with some embodiments of the invention that they may allow for only entering credential data, i.e. a password once and thus the user can use a password with a sever length and thus get a higher security level. Further, the user does not give away its biometrics, such as fingerprints, and the password is deleted from wristlet when removed from user. Further advantage is that the initial setup is easy with minimum interaction and the power consumption is neglect able.

Embodiments of the present disclosure will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference signs refer to like elements throughout. The terminology used herein is for the purpose of describing particular embodiments only and is not intended to be limiting of the invention.

As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

BRIEF DESCRIPTION OF THE DRAWINGS

Further objects, features and advantages of the present invention will appear from the following detailed description of the invention, wherein embodiments of the invention will be described in more detail with reference to the accompanying drawings, in which.

DETAILED DESCRIPTION

As used herein, the term "electronic device" includes portable communication device and portable radio communication equipment. Portable communication devices and mobile communication devices may be used synonymously. The term "portable radio communication equipment" may be referred to below as a mobile phone (or as a mobile telephone, portable phone or portable telephone), a portable device, a portable radio terminal or a portable terminal, includes all electronic equipment, including, but not limited to, capable of being used for voice and/or data communication.

As will be appreciated, the invention may be used with mobile phones, other phones, smartphones, personal digital assistants (PDAs), computers, other communication devices, etc., for brevity, the invention will be described by way of examples with respect to mobile phones, but it will be appreciated that the invention may be used with other communication devices.

Figure 1:
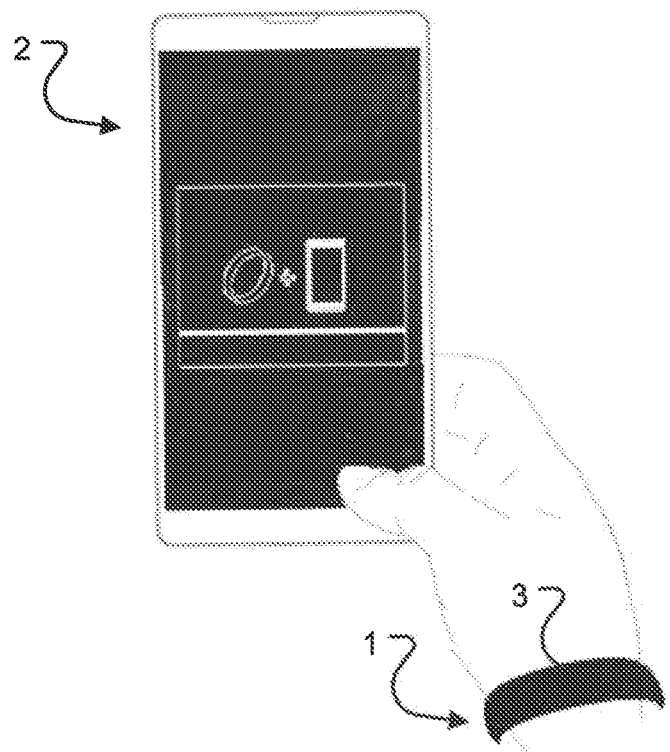
FIG. 1 discloses a view of a system comprising a wearable external device, e.g. a wristlet, and an electronic device, e.g. a mobile phone, according to the disclosure.
Figure 3:
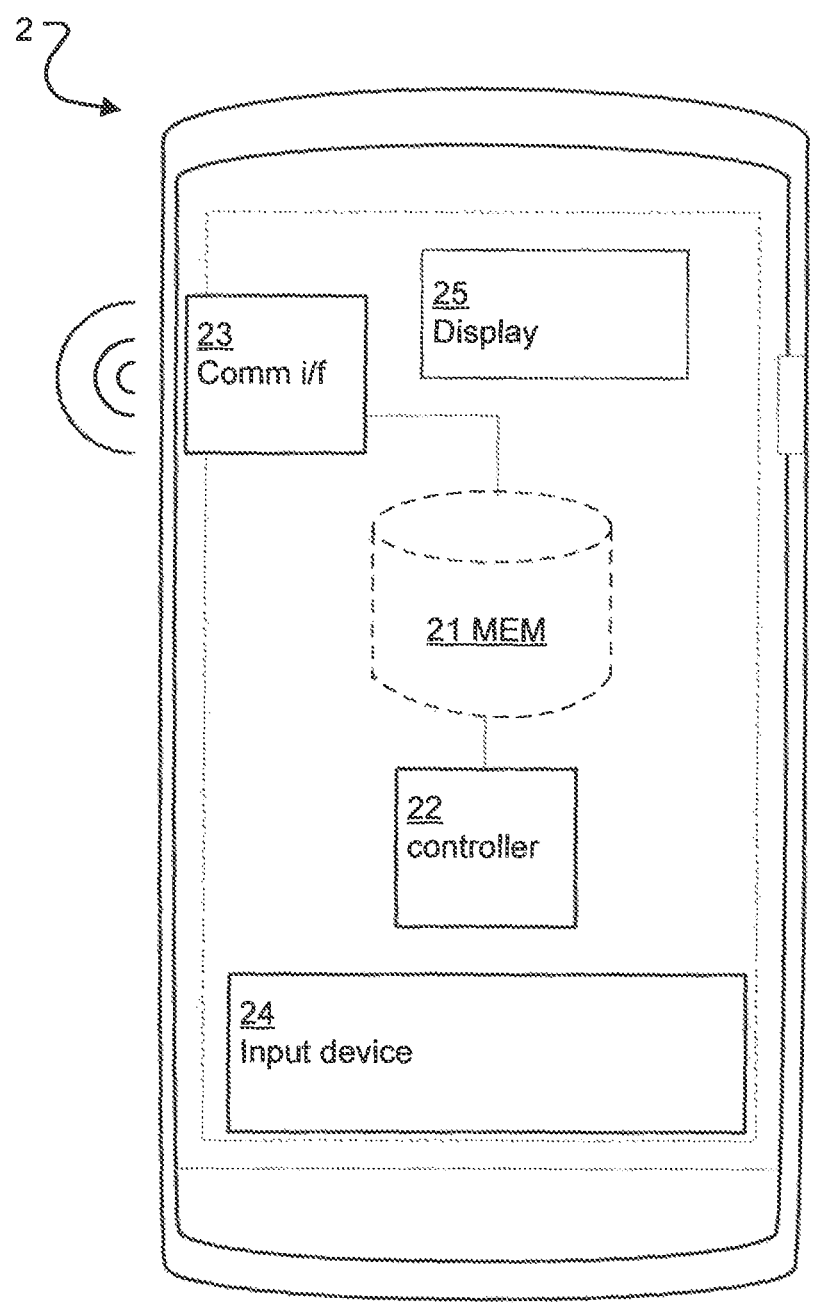
FIG. 3 discloses a block diagram of an electronic device, e.g. a mobile phone.

Referring in detail to the drawings, and initially to FIGS. 1 and 3, an electronic device in accordance with an embodiment of the present invention is illustrated generally at 2. The electronic device 2 will be referred to below as a mobile phone. However, as was mentioned above, references to "mobile phones" include various other devices, such as, for example, those mentioned above. In outward appearance, for example, as illustrated in FIG. 3, the mobile phone is of one type of design or style; however, the features of the invention, as are described in further detail below may be used in other types of mobile phones. The disclosure relates to the process for unlocking a mobile phone. This process could be eased up by having authorization data such as credential data, stored on a wearable external device.

The credential data can be encrypted. The credential data can be a random 128 bit hash code, which is set by the user. Thus the credential data can be very long if the user wants high security, since it only needs to be entered once.

A wearable external device 1 in this application refers to a device configured to be worn by a person, such as a wristlet or a watch.

In short, the disclosure provides for a wearable external device 1, i.e. a wristlet, and a method to implement a dynamic logon/logoff process for an electronic device 2, i.e. a mobile phone, by using the wearable external device 1, i.e. wristlet. The dynamic logon/logoff process starts by putting the wristlet 1 on a part of the body of the user, such as on the arm. The user will be prompted to send a key or a password to the wristlet 1, which is a signal that is sent to the mobile phone 2 from the wristlet 1 indicating that authentication data or credential data can be temporarily stored, when the user unlocks the mobile phone 2. The stored credential data could then be used for unlocking the mobile phone 2 as soon as the mobile phone 2 is within range of the wristlet 1. Thus, the wristlet is used as a personal ID device or key to the associated mobile phone 2, such that the mobile phone 2 is automatically unlocked when the wristlet 1 is close, within a range of 20-30 cm, to the mobile phone, without having to prompt the user to enter a password each time the user want to use the mobile phone 2. Thus, the user may continuously be able to use the mobile phone 2 without having to enter the password, as long as the wristlet 1 is on the arm of the user. The wristlet 1 is continuously detecting whether the wristlet 1 is on the arm and if the wristlet 1 is removed from the arm the dynamic logoff process starts by automatically clearing the stored credential data from the storage on the wristlet.

Thus, a system and method is provided where the user can choose an unlimited password, which may be cumbersome to enter, but which is rarely done, gives a high security level for usage of the electronic device and which does not risk the user to give away its biometrics.

According to one example embodiment the user puts on a wristlet on a body part, such as on the arm. The user then locks the wristlet around the arm with a lock, i.e. a snap lock. The user uses his mobile phone as he always does and he pushes a power button or presses a screen lock button and enters his password to unlock the mobile phone. This password can be very long if the user wants a high security level, and this is not a problem since the user only needs to enter it once when keeping the wristlet on the arm. The next time the user wants to unlock his mobile phone he only has to press the power button or screen lock button and the mobile phone opens without having to enter the password. When the user takes off the wristlet the connection between the wristlet and the mobile phone is lost and the next time the user wants to unlock or open his phone he has to enter the password as well.

Figure 4:
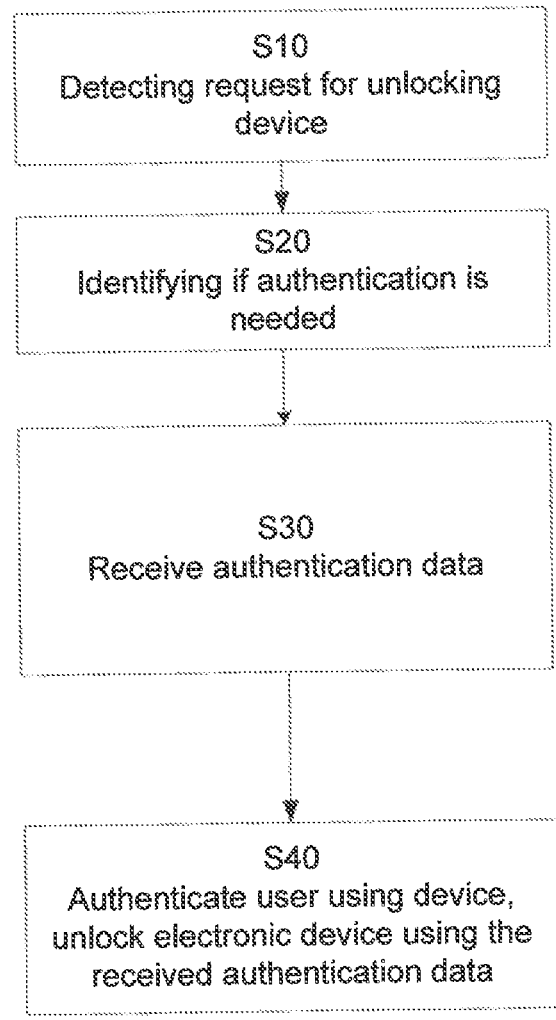
FIG. 4 discloses a flow chart of the method performed in an electronic device according to the disclosure.

The method will now be described starting from FIG. 4 disclosing method steps, performed in the mobile phone 2. When the described steps are not dependent on each other, these steps may be implemented in any combination.

In the first step the electronic device 2, e.g. mobile phone, detects S10 a request for unlocking the mobile phone 2, thus the user unlocks the mobile phone 2 by pressing the power on button on the mobile phone 2.

In the second step the mobile phone 2 identifies S20 if authentication is needed, when detecting power on S10.

In the third step the mobile phone 2 receives authentication data or credential data S30 for unlocking the mobile phone 2.

In the fourth step the mobile phone 2 is unlocked or opened S40 by using the received authentication data or credential data.

Figure 5:
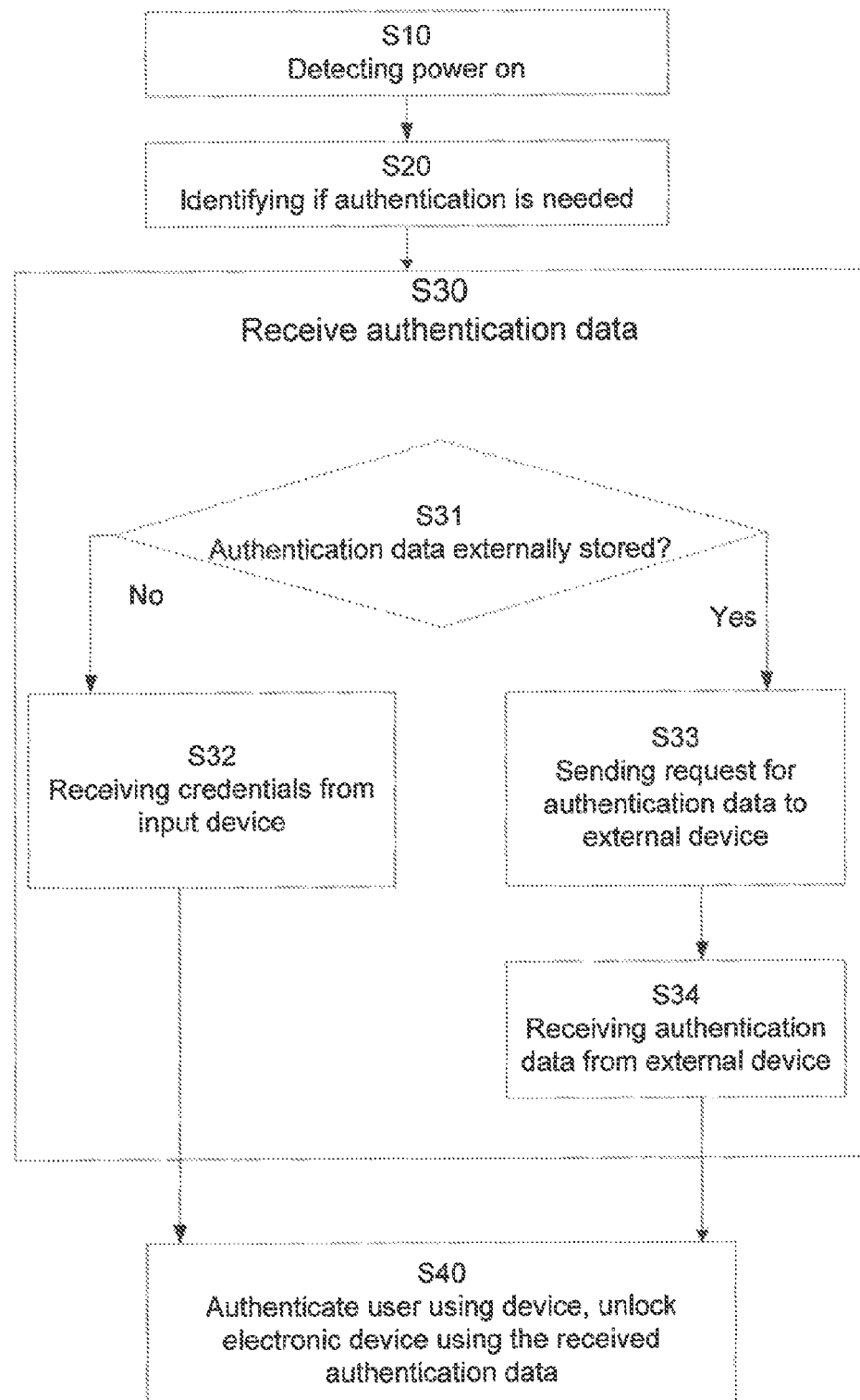
FIG. 5 discloses a flow chart of the method performed in an electronic device according to the disclosure.
Figure 6:
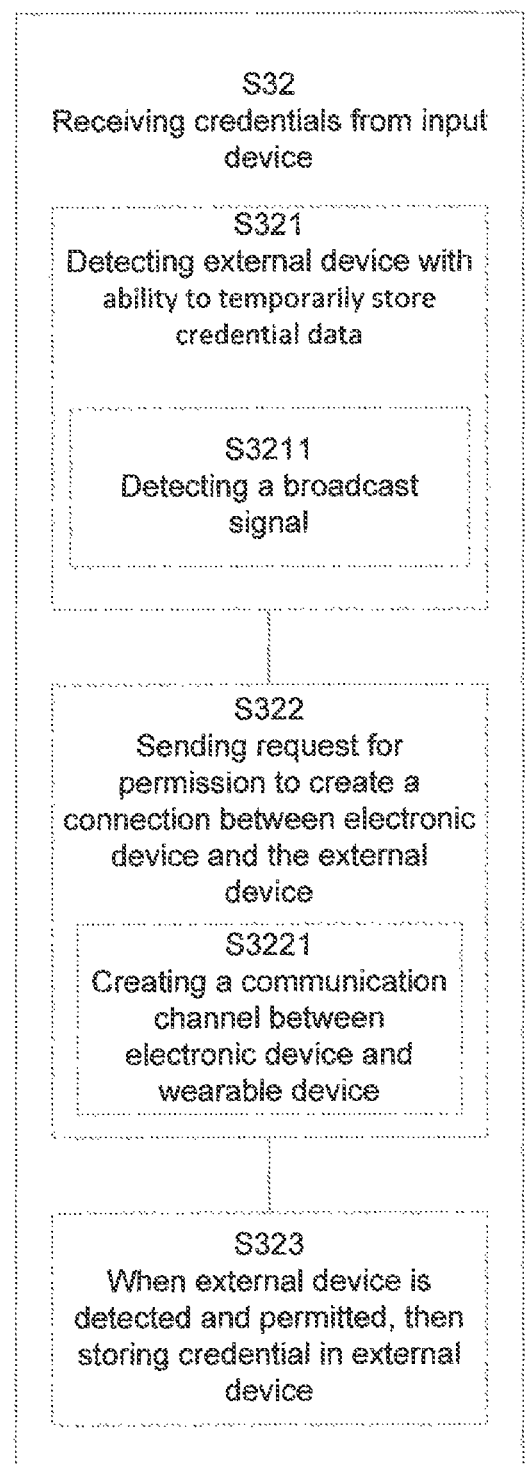
FIG. 6 discloses a flow chart of the method performed in an electronic device according to the disclosure.

FIGS. 5 and 6 discloses exemplary embodiments showing further variants and how the different steps of the method may be implemented in more detail. When the described aspects are not dependent on each other, these variants may be implemented in any combination.

According to one aspect the step of receiving S30 authentication data or credential data comprises identifying S31 whether the authentication data or credential data is stored externally, thus in a location outside the mobile phone, e.g. in a wearable external device nearby.

According to one aspect the step of identifying S31 whether the authentication data or credential data is stored externally or not, wherein no authentication data or credential data are externally stored. This is the case where the user unlocks his or her mobile phone the first time and then the method proceeds in the normal way. This is typically done by requesting and receiving S32 authentication data or credential data from an input device 24 of the mobile phone 2. The authentication data or credential data may e.g. be received from a user entering an alpha numeric password of unlimited length on an input device 24 of the mobile phone 2. According to one aspect of the step of receiving S32 authentication data or credential data from the input device 24, the steps further comprises entering a fingerprint on a touch screen comprised in the mobile phone. However, this disclosure then proposes to store the entered credentials in the mobile phone, such that the user will not need to reenter them the next time he or she wishes to unlock the mobile phone.

According to one aspect of the step of receiving authentication data or credential data S32 from an input device 24, the step further comprising the steps of detecting S321 an external device 1 with ability to store authentication data or credential data.

According to one aspect the step of detecting an external device 1 comprises detecting a broadcast signal S3211, indicating an ability to temporarily store authentication data or credential data.

According to one aspect the step of receiving credentials S32 from an input device 24 further comprises sending a request S322 for permission to create a connection between the detected wearable external device 1 and the mobile phone 2.

According to one aspect the step of sending a request S322 for permission to create a connection further comprises creating a communication channel S3221 between the mobile phone 2 and the wearable external device 1.

In one embodiment, the connection created in the step of creating a communication channel S3221 can be done by using Bluetooth Low Energy signal, BTLE, and the authentication data or credential data are transmitted to the wearable external device 1 when the wearable external device is detected and when transfer is permitted by the wearable external device. BTLE can be set to a limited distance, e.g. 40 cm to keep the battery long lasting. A small battery can last many months.

In one embodiment, the connection created in the step of creating a communication channel S3221 can be done by using NFC, e.g. by simply touching the wearable external device 1 with the mobile phone 2 and answering the question "transfer you credentials to this wristlet?" presented on a screen or a display 25 of the mobile phone 2 and the authentication data or credential data are then transmitted S323 to the wearable external device 1 when the wearable external device 1 is detected and when transfer is permitted by the wearable external device 1.

Alternatively, other radio information bearers can be used, such as Wi-Fi, Bluetooth, and Wireless charging. Alternatively, other transfer methods can be used, such as transfer through conductive, capacitive or inductive coupling.

According to one aspect the step of receiving credentials S32 from an input device 24 further comprises sending S323 authentication data or credential data for storage in the wearable external device 1, when the connection is created.

According to one aspect the step of identifying S31 whether the authentication data or credential data is stored externally or not, wherein the mobile phone detects that authentication data or credential data are already externally stored i.e. the steps S32-S323 have been executed, the mobile phone sends a request S33 for authentication data or credential data to the wearable external device 1, e.g. the wristlet.

According to one aspect the step of receiving authentication data the mobile phone 2 receives S34 authentication data or credential data from the wristlet 1. Once the authentication data or credential data are received from the wristlet 1, the authentication procedure may proceed according to the same procedure as when the authentication data or credential data where manually inserted.

In one embodiment, provided that the user has accepted or permitted sending a key, e.g. credential data, to the external device, the user will be notified once the key has been successfully transferred. When the user has accept sending the key to the external device the external device and the mobile will pair by using Bluetooth paring, BT pairing. This is done in the background, automatically without interference by the user. When the pairing is done, the key is sent from the mobile phone to the external device.

Figure 7:
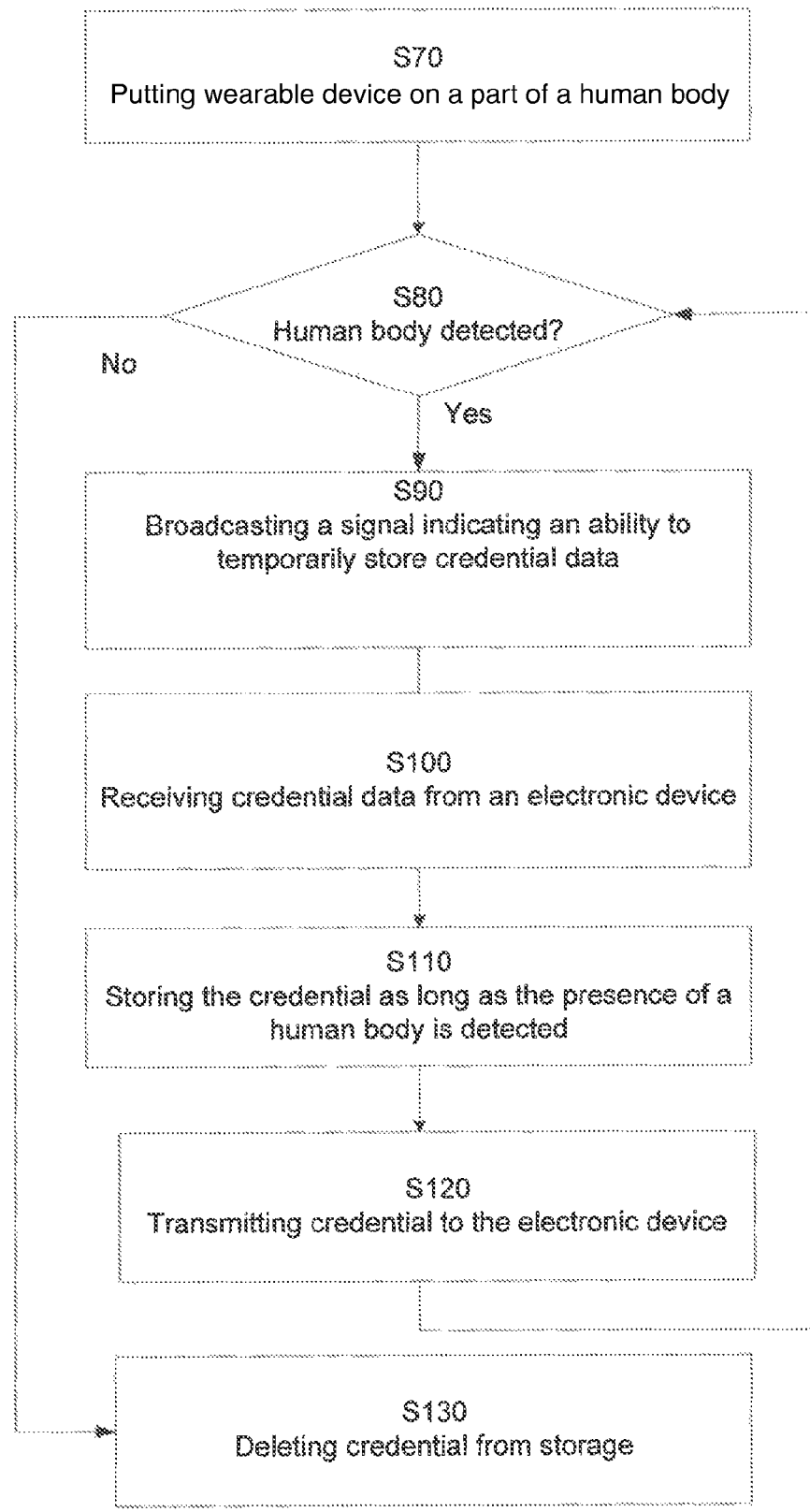
FIG. 7 discloses a flow chart of the method performed in a wearable external device according to the disclosure.

The method will now be described starting from FIG. 7 disclosing method steps, performed in the wearable device, i.e. the wristlet. When the described steps are not dependent on each other, these steps may be implemented in any combination.

In the first step the user puts S70 the wristlet 1 on a part of the body of the user, i.e. around his/her arm, and closes a magnetic, electric, optical or other loop i.e. strain gauges, capacitive, optic or other connection such that when the user removes the wristlet the loop must be broken. The size of the wristlet 1 should be such that it can't be taken off without breaking the loop. In one embodiment, the user may lock the loop around the part of the body with some kind of locking mechanism, such as a snap lock.

In the second step a detector unit 10 of the wristlet starts to detect S80 if the wristlet 1 is placed on a part of a human body, by detecting a tremor signal, pulse signal, a blood flow or a temperature change. When the wristlet has detected the presence of a human body it is activated. The wristlet is in a wristlet-on-a-human state.

In the third step S90, when the wristlet is activated, a controller 12 of the wristlet starts to broadcast a signal, indicating an ability to temporarily store credential data.

In one embodiment the broadcast signal is a Bluetooth Low Energy signal, BLTE. BLTE can be set to a limited distance, i.e. 40 cm to keep the battery long lasting.

In the fourth step S100 the wristlet receives, using a radio communication interface 11, authentication data or credential data from the mobile phone 2.

In the fifth step S110 the wristlet stores, in data storage 13, the received authentication data or credential data in the data storage as long as the detector unit 10 detects the presence of a human body.

In the sixth step S120 the wristlet 1 transmits the authentication data or credential data to the electronic device 2, when a request for credentials is received. The wristlet is in a wristlet-of-human state.

In one embodiment, the method further comprises the steps of deleting S130 the credentials when the presence of a human body is no longer detected.

In one embodiment, when the user wears the wristlet and pushes the power button on the mobile phone, there is no password needed, since it is sent from the wristlet. When it is concluded that the wristlet is on a body part of the user, such as an arm, BT low energy is turned on for broadcast. When the user unlocks the mobile phone, the broadcasted low energy signal will be detected. If the wristlet is close enough, e.g. within a distance of 30 cm, the mobile phone will send a request for the key, e.g. credential data. The key are then transferred to the mobile phone 2 and then the mobile phone 2 is unlocked. If there are no key in the wristlet, which is the case the first time the user logon to the mobile phone after putting on the wristlet, the mobile phone will request a key from the user, with UI on the screen of the mobile phone, asking for a key and asking if the user wants to transfer a key to the wristlet or not.

In one embodiment, as a power saving feature, the wristlet-on-a-human detection should serve as a trigger for sampling detection data over a short period to determine if the wristlet has been activated while on a human body part. This is only done once per wristlet-on-a-human detection period.

As soon as a successful wristlet-on-a-human detection is done the detector needs to be reconfigured to generate a stationary/complete-still interrupt towards its host system. This is done as a pre-caution in case of having the wristlet removed from the body part without detecting wristlet-of-a-human.

The wristlet can be used with other electronic devices, such as laptop, PlayStation controller.

In one embodiment, the wristlet is used with a laptop, the laptop may be unlocked, according to the method presented above, when the user puts his arm with the wristlet on the key board.

In one embodiment, the wristlet is used with a PlayStation controller, the PlayStation controller identifies the user when the user with a wristlet holds the PlayStation controller, according to the method presented above. Similar scenario can be when login to PlayStation or PSN.

In one embodiment, it is possible to store other information than just the credential data on the wristlet, e.g. the mobile phone 2 can send the phone ID to be stored on the wristlet 1 such that when the user is about to login to the PlayStation network, the user is suggested to login with the same ID. Alternatively, when several users play the same game, the ID from their wristlets is used for their identity in the game.

In one embodiment, the wristlet 1 can also be used to unlock your home if you have sent your unlock-home-ID to be stored on your wristlet 1. You can then open the door by just putting your hand with the wristlet on the handle. This can also be used when performing payments on the internet.

In one embodiment, the wristlet 1 can also be used for secure login to your bank, from your PC, i.e. in Sweden the Mobile Bank ID is used to do payments from your bank and many people chooses relatively shorts passwords since it is cumbersome to enter a long password. The wristlet can also be used for NFC payment in shops.

In one embodiment, if there are several users that knows the password to the electronic device 2, every time the electronic device 2 is unlocked with the password, an authorization question, i.e. "would you like your wristlet to be used as a key to your device?", should be asked, provided the user is wearing a wearable device according to the disclosure, i.e. a wristlet.

In one embodiment, when using a family tablet at home, all the members of the family can use it together with their wristlets, without having to enter the credential data or password. The look of the display may also be customized, i.e. display a personalized message, such as "welcome Henrik", or "welcome Anna", and it can remember what applications that the member last used.

In one embodiment, the wristlet can be connected to several electronic devices at the same time, with the same password or several different passwords, dependent on the electronic device. For example, the user may connect the wristlet to the phone using a first password and to connect with the computer with a second password. All the passwords are stored in the wristlet.

When the user takes off the wristlet 1 the connection is broken, both through electro-mechanical disconnect and though loss of detection of a human body. All connecting information is lost, all data on the wristlet is removed, the wristlet is inactivated and thereafter the wristlet cannot be used to open the phone. The inactivated wristlet has no value other than its hardware when it is taken off, since it has no memory. Thus, when the wristlet is not on a human body part, the user can be sure that it carries no information, and all data is removed.

Figure 2A:
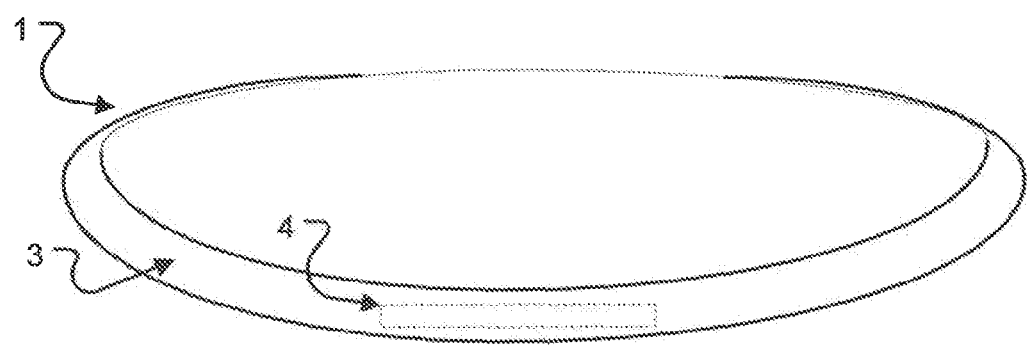
FIG. 2a discloses a block diagram of a wearable external device, e.g. a wristlet, according to the disclosure.
Figure 2B:
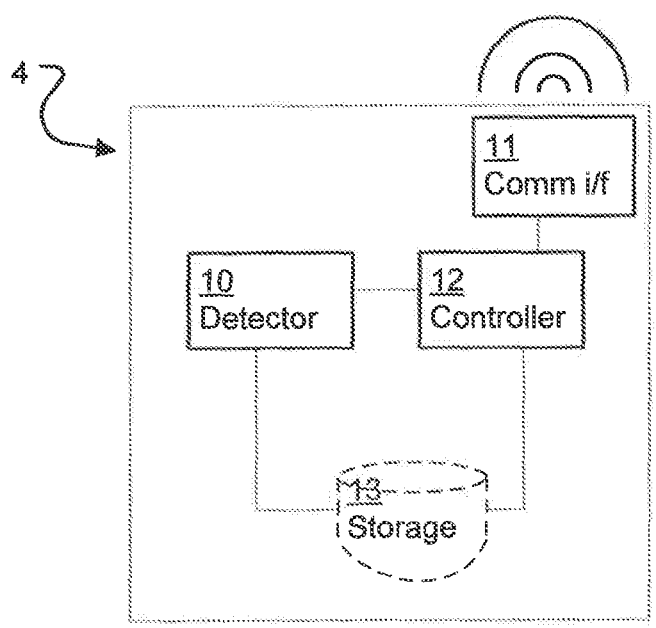
FIG. 2b discloses a block diagram of an electronic module comprised in a wearable external device, according to the disclosure.

FIG. 1 show a wearable external device 1, which now will be described in further detail, configured for temporarily storing credentials associated with at least one electronic device 2, where the method is implemented. The wearable external device 1 is configured to be wearable, thus it can be worn on a part of the human body of the user, such as on or around a wrist, arm or neck, as long as it is in close contact, preferable within a range of 20-30 mm, with the skin of the human body. The wearable external device 1 in FIG. 1 comprises a wearable unit 3 and an electronic module 4 placed in said wearable unit, as shown in FIGS. 2a and 2b. The electronic module 4 is designed to be removed from the wearable unit and put in another wearable unit. The wearable unit 3 can be designed as a wristband, wristlet, bracelet, bangle, necklace, collar, a watch or the like. The wearable external device 1 can also be attached onto the skin of the user, such as a patch or any adhesive or sticking piece of paper or plastic. The wearable external device 1 may also be attached to the clothes worn by the user. However, for the sake of clarity and simplicity, most embodiments outlined in this specification are related to a wristlet 1 comprising a wrist band 3 holding the electronic module 4.

FIGS. 2a and 2b shows the electronic module 4 configured for temporarily storing credentials associated with at least one electronic device 2, where the method is implemented. The electronic module 4 comprises a detector unit 10 configured to detect the presence of a human body. The detector 10 can be a sensor of any kind such as an accelerator, optical sensor, temperature sensor, pulse sensor or the like. The detector unit can be placed on the back of the wrist band 3.

In one embodiment the detector unit comprises a capacitive touch system. The capacitive touch system is placed on the back of the wrist band 3 that is on the part of the wearable unit 3 that is closest to the body part of the user, which is wearing the wristlet 1. The capacitive touch system has low power consumption, which is less than 30 micro Amp when the wristlet is on a body part as well as of a body part. The sensitivity range may be set to the range of 20-30 mm, such that the wristlet 1 may be loosely coupled around a body part, such as an arm, and still give a signal. The capacitive sensor system is always active.

As soon as the wristlet 1 is placed on a part of the human body of the user, such as around the arm or wrist, the detector unit 10 starts to sense the presence of a human body.

In one embodiment, the detector unit 10 comprises an accelerometer, which can detect a tremor signal from the user. A tremor signal is a signal measuring the human quiver or tremble movement and it is always present in human muscles at a frequency of 8-12 Hz.

In one embodiment, the detector unit 10 comprises a pulse sensor, which can detect the heart rate or blood pulse of the user.

In one embodiment, the detector unit 10 comprises a temperature sensor, which can detect the temperature of the skin of the user.

In one embodiment, the detector unit 10 comprises an optical sensor, which can detect the blood flow of the user.

The electronic module 4 further comprises a controller 12. The controller is configured to execute the method according to the disclosure. The controller 12 is typically a processing circuitry configured for executing computer code, such as a computer program implementing the proposed method. One example is that the computer code is an application, which may be downloaded from an external server. However, the method may as well be hardware implemented or a combination of hardware and software. The controller 12 is configured for broadcasting a signal S90, as shown in FIG. 7, indicating an ability to temporarily store credential data, when the detector unit 10 detects S80 the presence of a human body.

The electronic module 4 further comprises a radio communication interface 11 configured to communicate with at least one electronic device 2. The controller 12 is configured to receive S100, using the radio communication interface 11, authorization data or credential data from the electronic device 2.

The electronic module 4 further comprises a data storage 13 configured to store the authorization data or credential data. The controller 12 is configured to store S110, in the data storage 13, the received credentials as long as said detector unit 10 detects the presence of a human body and to transmit S120 the credentials to the electronic device 2, when a request S33, as shown in FIG. 5, for credential data is received.

The controller 12 is further configured to remove S130 the credentials from the storage 13 when the presence of a human body is no longer detected.

In one example embodiment, a specific application, an app, is started in the mobile phone and the app chooses which authorization data to enter, such as to use a password, a fingerprint, other biometrics, such as iris recognition, tremble identification (tremor signal), voice recognition or other as authorization data.

In one embodiment, the detector unit 10 comprises a capacitive touch system and an accelerometer. When the wristlet 1 is placed on an arm the capacitive touch system will send an interrupt signal to the controller comprised in the electronic module 4, informing the controller that the wristlet is placed on an arm, or something with a similar capacitance as an arm. Then the accelerator starts to detect a tremor signal. If the tremor signal is found, it is concluded that the wristlet is put on an arm. The capacitive touch system is always active, and when the system detects that the signal is lost it will send an interrupt signal to the electronic module 4.

FIG. 3 shows the electronic device, e.g. the mobile phone 2, which now will be described in further detail. The mobile phone 2 comprises a controller, CTL, or a processing circuitry 22 that may be constituted by any suitable Central Processing Unit, CPU, microcontroller, Digital Signal Processor, DPS, etc. capable of executing computer program code for executing the method disclosed. However, the method may as well be hardware implemented or a combination of hardware and software. The computer program may be stored in a memory 21, MEM. The memory can be any combination of a Read And write Memory, RAM, and a Read Only Memory, ROM. The memory 21 may also comprise persistent storage, which, for example, can be any single one or combination of magnetic memory, optical memory, or solid state memory or even remotely mounted memory.

The mobile phone 2 further comprises a wireless communication interface (i/f) 23 arranged for wireless communication with cellular communication system and/or other wireless communication systems. The wireless communication interface 23 may be adapted to communicate over one or several radio access technologies. If several technologies are supported, the access point typically comprises several communication interfaces, e.g. one WLAN communication interface and one cellular communication interface. The communication interface is e.g. adapted to download a computer program for executing the proposed methods or access a data base comprising device specific information.

The foregoing has described the principles, preferred embodiments and modes of operation of the present invention. However, the invention should be regarded as illustrative rather than restrictive, and not as being limited to the particular embodiments discussed above. The different features of the various embodiments of the invention can be combined in other combinations than those explicitly described. It should therefore be appreciated that variations may be made in those embodiments by those skilled in the art without departing from the scope of the present invention as defined by the following claims.

The invention claimed is:

1. A wearable device for temporarily storing credential data associated with at least one electronic device comprising:
    a detector unit configured for detecting the presence of a human body;
    a radio communication interface configured to communicate with the at least one electronic device;
    a data storage configured to store the credential data;
    a processing circuitry configured:
        to broadcast a signal, indicating an ability to temporarily store credential data, when said detector unit detects the presence of a human body;
        to receive, using the radio communication interface, the credential data from said electronic device;
        to store, in the data storage, the received credential data in the data storage as long as said detector unit detects the presence of a human body, and
        to transmit the credential data to the electronic device, when a request for credentials is received.

2. The device according to claim 1 wherein said processing circuitry is configured to delete the credential data when the presence of a human body is no longer detected.

3. The device according to claim 1 wherein said processing circuitry is configured to receive encrypted credential data.

4. The device according to claim 1 wherein said device further comprises an electronic module and a wearable unit.

5. The device according to claim 4 wherein said electronic module comprises said radio communication interface, said data storage and said processing circuitry.

6. The device according to claim 4 wherein said electronic module further comprises said detector unit.

7. A method, performed in a wearable device, of temporarily storing credentials associated with at least one electronic device within the wearable device, the method comprising the steps of:
    broadcasting a signal, indicating an ability to temporarily store credential data, when the presence of a human body is detected by a detector unit;
    receiving, using a radio communication interface, credential data from said electronic device,
    storing, in a data storage, the received credentials in the data storage as long as said detector unit detects the presence of a human body, and
    transmitting the credential data to the electronic device, when a request for credential data is received.

8. The method according to claim 7, wherein said method further comprising the steps of:
    deleting the credential data when the presence of a human body is no longer detected.

* * * * *